United States Patent
Silverman

(10) Patent No.: US 10,046,052 B2
(45) Date of Patent: Aug. 14, 2018

(54) METHOD AND FORMULATION FOR COLD TREATMENT IN ADULTS AND CHILDREN WITH INCREASED SAFETY

(76) Inventor: Bernard Silverman, Cedarhurst, NY (US)

( * ) Notice: Subject to any disclaimer, the term of this patent is extended or adjusted under 35 U.S.C. 154(b) by 62 days.

(21) Appl. No.: 13/108,964

(22) Filed: May 16, 2011

(65) Prior Publication Data

US 2011/0281892 A1 Nov. 17, 2011

Related U.S. Application Data

(60) Provisional application No. 61/334,613, filed on May 14, 2010.

(51) Int. Cl.

| | |
|---|---|
| *A61K 31/495* | (2006.01) |
| *A61K 31/09* | (2006.01) |
| *A61K 31/167* | (2006.01) |
| *A61K 31/192* | (2006.01) |
| *A61K 31/445* | (2006.01) |
| *A61K 31/4545* | (2006.01) |
| *A61P 29/00* | (2006.01) |
| *A61K 45/06* | (2006.01) |

(52) U.S. Cl.
CPC ............ *A61K 45/06* (2013.01); *A61K 31/09* (2013.01); *A61K 31/167* (2013.01); *A61K 31/192* (2013.01); *A61K 31/445* (2013.01); *A61K 31/4545* (2013.01); *A61K 31/495* (2013.01)

(58) Field of Classification Search
CPC .. A61K 2300/00; A61K 31/09; A61K 31/167; A61K 31/192; A61K 31/445; A61K 31/4545; A61K 31/495; A61K 45/06
See application file for complete search history.

(56) References Cited

U.S. PATENT DOCUMENTS 4,783,465 A * 11/1988 Sunshine et al. .......... 514/225.8

OTHER PUBLICATIONS

Ogbru et al., 2007, p. 1-3.*
Cetirizine document, p. 1-7, 2009.*
Brady Health Center Document (Brady Health Center, Frostburg State University, 2008).*
ICSI document (Diagnosis and Treatment of Respiratory Illness in Children and Adults, 2nd Edition, Jan. 2008).*
Acetaminophen (http://www.dailymed.nlm.nih.gov/dailymed/archives/fdaDrugInfo. cfm?archiveid=19077).*
Nathan (http://www.medscape.com/ yiewarticle/708927_5, 2009).*
Lambert, (Am Fam Physician, Jul. 1, 2009 80(1), 79-85).*
Ciprandi et al. (Allergy, 1997, 52, 752-754).*

\* cited by examiner

*Primary Examiner* — Umamaheswari Ramachandran
(74) *Attorney, Agent, or Firm* — Israel Nissenbaum; Yitzy Nissenbaum

(57) ABSTRACT

Methods and dosage formulations for the safe treatment of cold, cough, flu, and sinus symptoms in children and adolescents by age and nature of symptoms, and adults and the elderly by age, nature of symptoms, and concomitant patient medical conditions. The method of the present invention comprises the formulation of a cold medication which consists essentially of combinations of a nonsedating or minimally sedating antihistamines with pain relievers and the expectorant, guaifenesin.

1 Claim, No Drawings

METHOD AND FORMULATION FOR COLD TREATMENT IN ADULTS AND CHILDREN WITH INCREASED SAFETY

FIELD OF THE INVENTION

This invention relates to methods and formulations for safely treating colds in adults and the elderly, and methods and formulations for safely treating colds in children, and particularly to methods and formulation for effective cold treatments which are physiologically safe according to recognized standards.

BACKGROUND

A plethora of cold, cough, flu, and sinus relief products in various pharmaceutical combinations are marketed worldwide, with revenue projected to exceed $22.2 billion by the year 2015. This is primarily driven by a rise in the population suffering from cold, cough, and sore throat symptoms, and the introduction of effective medications.

School children are three times more susceptible to cold and cough than average adults due to underdeveloped immune systems and close contact with each other in the classroom. Colds increase during school re-opening in September and in winter.

On average, each year about one billion colds are reported and 17% of the population is infected with flu virus. Patients with heart disease, asthma, diabetes, pregnant women, the elderly, and young children are at a higher risk of exposure to flu related complications. It is estimated that about 35,000 people die each year due to flu related complications in the United States.

Nearly all cough and cold preparations contain sympathomimetic decongestants (i.e. pseudoephedrine, phenylephrine, phenypropanolamine); and pain relievers (i.e. acetaminophen, ibuprofen); and many contain sedating antihistamines (i.e. diphenhydramine, chlorpheniramine, doxylamine), dextromethorphan; and/or guaifenesin (an expectorant).

Adverse effects, particularly associated with the decongestant component, but also dextromethorphan and the sedating antihistamines have prompted the U.S. Food and Drug Administration (FDA) to recommend that Over-the-Counter (OTC) cough and cold products not be used for infants and children under 2 years of age because "serious and potentially life-threatening side effects can occur".

The FDA has not completed its review of information about the safety of OTC cough and cold medicines in children 2 through 11 years of age, but there are reports of serious side effects including death resulting from use of cough and cold medicines in children 2 years of age and older. Also, according to the American Academy of Pediatrics, "several studies show that cold and cough products don't work in children younger than 6 years and can have potentially serious side effects". Due to this, an FDA panel voted that cold medicine should not be used by children under 6 and although nonbinding, package labels do not recommend their use in this age group.

Decongestants, sedating antihistamines, and dextromethorphan also have significant adverse effects in adults.

Decongestants constrict blood vessels and exert effects on smooth muscle throughout the body, directly stimulate the heart and brain, dry airway secretions, and affect blood sugar. Therefore, they are generally not recommended for people with heart disease, high blood pressure, glaucoma, thyroid disease, urinary retention problems, seizure disorders, asthma, or diabetes.

They should generally not be taken with caffeine, stimulant diet pills, or monoamine oxidase inhibitors, among other drugs.

Common side effects include nervousness, restlessness, excitability, dizziness, headache, nausea, weakness, drowsiness or trouble sleeping and rapid heart beat. Patients may also experience increased blood pressure, irregular heartbeat, severe headache, tightness or discomfort in the chest, breathing problems, fear or anxiety, hallucinations, trembling or shaking, convulsions (seizures), pale skin, or painful or difficult urination.

Phenylpropanolamine (PPA), used in many products in the past, is now avoided due to possible risk of stroke.

Pseudoephedrine, once a common over-the-counter decongestant, is available only after consultation with a pharmacist in many states, since it is used to make illegal methamphetamine.

Sedating antihistamines can cause drowsiness, dizziness, and blurred vision, all of which could lead to motor vehicle and other accidents, particularly falls and fractures in the elderly. Other adverse effects include headache, loss of appetite, dry mouth, constipation, difficulty passing urine and confusion. These drugs are not recommended for people with glaucoma, enlarged prostate, high blood pressure, or seizure disorder, and should not be taken with anti-depressant, sedative, hypnotic, or tranquilizer medications.

Millions of Americans use dextromethorphan safely each year to relieve cough symptoms due to the common cold or flu. It is a non-narcotic, non-addictive cough suppressant which raises the coughing threshold in the brain and has no pain relieving properties. However, dextromethorphan may cause dizziness, lightheadedness, drowsiness, nervousness, restlessness, nausea, vomiting, and stomach pain. In addition, users of dextromethorphan may cause severe allergic reactions (rash; hives; difficulty breathing; tightness in the chest; swelling of the mouth, face, lips, or tongue). Furthermore, some teenagers and young adults intentionally abuse large amounts of preparations containing dextromethorphan in order to get high.

The myriad of adverse effects in various patient populations and the small potential benefit of these drugs (symptomatic relief only) versus their significant potential risk should merit exclusion of all in cold, cough, flu, and sinus preparations for children and specifically decongestants in all adults. Sedating antihistamines and dextromethorphan should also be excluded in the elderly. However, it was believed that exclusion of the sedating antihistamines and the decongestants would severely lessen or eliminate effectiveness of formulations used to treat cold, cough, flu and particularly sinus symptoms.

SUMMARY OF THE INVENTION

It is accordingly an object of the present invention to provide a safe, yet surprisingly effective age specific method with an age specific treatment formulation for treating cold, cough, flu, and sinus symptoms even in infants 6 months and older, children and adolescents. Age appropriate use in the method and formulation comprise combinations consisting essentially of a nonsedating or minimally sedating antihistamine, pain reliever, and guaifenesin, with omission of the pain reliever and guaifenesin components, based on specific patient symptom and age criteria.

It is a further object of the present invention to provide a safe method and formulation for treating cold, cough, flu, and sinus symptoms in adults and the elderly essentially using active ingredients of only an age and medical condition appropriate nonsedating or minimally sedating antihistamine, pain reliever, and guaifenesin.

Generally the present invention comprises methods and formulations for the safe treatment of cold, cough, flu, and sinus symptoms in children and adolescents by age and nature of symptoms, and adults and the elderly by age, nature of symptoms, and concomitant patient medical conditions. The method of the present invention comprises the formulation of a cold medication which consists essentially of combinations of a nonsedating or minimally sedating antihistamines with pain relievers and the expectorant, guaifenesin. These components are specifically:

i) A non-sedating or minimally sedating antihistamine and specifically cetirizine, levocetirizine, desloratadine, loratadine, fexofenadine, and safe equivalents thereof;
 ii) A pain reliever and specifically ibuprofen and acetaminophen, and safe equivalents thereof;
 iii) Guaifenesin;
 iv) Decongestants, dextromethorphan and sedating antihistamines are specifically excluded.

The method and formulation, as described, and with a specific non-sedating or minimally sedating antihistamine, with or without pain relievers and/or guaifenesin, appropriate for a patient having any or all of a cold, cough, flu, and sinus symptoms according to age group, and medical condition susceptibilities, is safely given to the patient in an appropriate dose or doses. Surprisingly, the method and formulations, even without decongestants, strong sedating antihistamines and dextromethorphan has been clinically demonstrated as providing effective symptom relief, without concomitant safety issues.

DETAILED DESCRIPTION OF THE INVENTION

The method for the safe treatment in infants 6 months or older, children, and adolescents comprises the steps of excluding from the formulation, decongestants, sedating antihistamines, and dextromethorphan and including in the formulation, as age appropriate; combinations of a nonsedating or minimally sedating antihistamine alone or with pain relievers, and/or guaifenesin and administering the appropriate formulation based on symptoms to a child or adolescent, in need thereof, in dosage appropriate amounts. In younger children, guaifenesin is omitted.

The method for the safe treatment of colds, coughs, flu, and sinus symptoms in adults comprises the steps of excluding from the formulation, decongestants and sedating antihistamines and providing combinations of a nonsedating or minimally sedating antihistamine alone, or with pain relievers, and/or guaifenesin based on specific patient symptom(s).

The method for the safe treatment of colds, coughs, flu, and sinus symptoms in elderly adults comprises the steps of excluding from the formulation, decongestants, sedating antihistamines, and dextromethorphan and providing combinations of a nonsedating antihistamine alone, or with pain relievers, and/or guaifenesin based on symptoms.

The specific (though not limiting) formulations of the present invention consist essentially of combinations of the following components:

a) a nonsedating antihistamine and most preferably cetirizine, levocetirizine, desloratadine, loratadine and fexofenadine according to age:
   i) Six months to two years—cetirizine, or desloratadine;
   ii) Two to seventy years—cetirizine, desloratadine, loratadine and fexofenadine;
   iii) Six to seventy years—cetirizine, desloratadine, loratadine, fexofenadine and levocetirizine.
   iv) Seventy years and above and those with liver or kidney disease—fexofenadine
 b) Pain relievers and most preferably acetaminophen and ibuprofen according to age:
   i) Six months to seventy years—acetaminophen or ibuprofen
   ii) Seventy and above years—acetaminophen
   iii) patients with kidney, gastroesophageal, or bleeding disorders—acetaminophen
   iv) patients with liver disease—ibuprofen
 c) Guaifenesin: Six to above seventy years Specific Safe and Effective Combination Formulations:

The following formulations of a minimally sedating antihistamine, Cetirizine, with and without pain relievers have been clinically found to be both safe and effective in the treatment of colds, coughs, flu, and sinus symptoms in various age groups and in controlled dosages:

Cetirizine 5 mg per 5 ml (1 teaspoonful), 5 and 10 mg Tablets
Cetirizine 5 mg/Ibuprofen 100 mg per 5 ml Syrup
Cetirizine 5 mg/Ibuprofen 200 mg Tablets
Cetirizine 10 mg/Ibuprofen 200 mg Tablets
Cetirizine 5 mg/Acetaminophen 160 mg per 5 ml Syrup
Cetirizine 5 mg/Acetaminophen 325 mg Tablets
Cetirizine 10 mg/Acetaminophen 325 mg Tablets Safe and Effective Dosing The above formulations have been found to have both safety and efficacy when used in the following dosing regimens as applied to age specific patients:

Children 6-23 months: The recommended starting dose is ½ a teaspoonful once a day. For children 12-23 months, may be increased to ½ a teaspoonful every 12 hours.

Children 2-5 years: The recommended starting dose is ½ a teaspoonful once a day. May be increased to a maximum of 1 teaspoonful once a day, or ½ a teaspoonful every 12 hours. Cetirizine is not recommended in children <6 years old with kidney or liver problems.

Children 6 years and over: 5-10 mL (1-2 tsp) once to twice daily depending upon severity of symptoms. Max: 10 mL, (2 tsp)/day.

Adults and Children 6 years and over: One 10 mg tablet once daily; do not take more than one 10 mg tablet in 24 hours. A 5 mg product (tablet or syrup) may be appropriate for less severe or more frequent symptoms. 5-10 mg (1-2 tab or 5-10 mL (1-2 tsp) once to twice daily depending upon severity of symptoms. Max: 10 mg (2 tab) or 10 mL (2 tsp) per day.

Specific Safe and Effective Combination Formulations:

The following formulations of a minimally sedating antihistamine, Cetirizine, with Guaifenesin have been clinically found to be both safe and effective in the treatment of colds, coughs, flu, and sinus symptoms in various age groups and in controlled dosages:

Cetirizine 5 mg/Guaifenesin 100 mg per 5 ml Syrup
Cetirizine 5 mg/Guaifenesin 100 mg Tablets
Cetirizine 10 mg/Guaifenesin 100 mg Tablets
Cetirizine 5 mg/Guaifenesin 100 mg/Ibuprofen 100 mg per 5 ml Syrup
Cetirizine 5 mg/Guaifenesin 100 mg/Ibuprofen 200 mg Tablets Cetirizine 10 mg/Guaifenesin 100 mg/Ibuprofen 200 mg Tablets
Cetirizine 5 mg/Guaifenesin 100 mg/Acetaminophen 160 mg per 5 ml Syrup
Cetirizine 5 mg/Guaifenesin 100 mg/Acetaminophen 325 mg Tablets
Cetirizine 10 mg/Guaifenesin 100 mg/Acetaminophen 325 mg Tablets Safe and Effective Dosing The above formulations have been found to have both safety and efficacy when used in the following dosing regimens as applied to age specific patients:

Children 6 years and over: 5 mL (1 tsp) once to twice daily depending upon severity of symptoms. Max: 10 mL (2 tsp)/day.

Adults and Children 6 years and over: One 10 mg tablet once daily; do not take more than one 10 mg tablet in 24 hours. A 5 mg product (tablet or syrup) may be appropriate for less severe or more frequent symptoms. 1 tab or 5 mL (1 tsp) once to twice daily depending upon severity of symptoms. Max: 10 mg (2 tab) or 10 mL (2 tsp)/day.

The above combinations and dosing are similarly applicable to the non-sedating antihistamine, Desloratadine, wherein 2.5 mg and 5 mg dosages are substituted for Cetirizine 5 and 10 mg dosages respectively.

The above combinations and dosing are similarly applicable to the non-sedating antihistamine, Loratadine, wherein 5 mg and 10 mg dosages are substituted for Cetirizine 5 and 10 mg dosages, respectively and wherein the patient is 2 years or older.

The above combinations and dosing are similarly applicable to the non-sedating antihistamine, Fexofenadine, wherein 30 mg and 60 mg dosages are substituted for Cetirizine 5 and 10 mg dosages respectively and the dose for children 2 through 11 years old is 1 teaspoonful twice daily. A Fexofenadine dosage of 180 mg may be substituted for Cetirizine 10 mg tablet wherein the patient is 12 years and older.

The above combinations and dosing are similarly applicable to the minimally sedating antihistamine, Levocetirizine, wherein dosages of 2.5 mg and 5 mg are substituted for Cetirizine 5 and 10 mg dosages, respectively, wherein the patient is 6 years or older and wherein the maximum dose for 6 to 12 years is 2.5 mg per day.

It should be noted that the pain reliever (anti-pyretic) dose in these preparations may not be sufficient in quantity or frequency to reduce significant fever. In such situations this component may need to be used separately.

Safety of Components

Non or minimally sedating antihistamines (e.g., cetirizine, levocetirizine, fexofenadine, loratadine, desloratadine) have been proven safe and effective for allergic conditions in children as young as 6 months with minimal adverse effects and medication interactions. There is limited to no experimental evidence, but much practical experience demonstrating efficacy of these drugs for nasal symptoms associated with upper respiratory infection. Besides no or low sedation, all have less anticholinergic effects than sedating antihistamines, and hence do not cause significant drying of secretions, a particular benefit in lower respiratory infection and asthma, which can complicate upper respiratory infection.

Pain relievers such as acetaminophen and ibuprofen are generally safe in children and adults when used at appropriate doses, time intervals, and for short periods. Ibuprofen and other NSAID's may however be contraindicated with conditions such as gastrointestinal, renal, or potential bleeding problems and acetaminophen with liver disease.

Guaifenesin, a mucolytic or expectorant, is safe in children and adults at appropriate doses.

In summary, these three classes of drugs are used alone or in various combinations in children 6 months and above and adults at appropriate preparations and doses for age, symptoms, and concomitant medical disorders. Only non sedating antihistamines, acetaminophen, and guaifenesin are used in the elderly.

Examples with Efficacy of Method and Formulation Treatment:

Though the above formulations are not known as fixed dose combinations, the examples provided herein are based on safety and efficacy when used together as separate preparations, thus presumed safe and effective as a combination drug.

The following specific formulations have been shown to be used in effective and safe cold treatment regimen and formulation usage according to the present invention and according to age specific criteria:

1. Infants & Young Children Up to Two Years Old:
E.g., one year old with upper respiratory infection, fever, and nasal congestion:
Effectively treated with a combination: Cetirizine and Acetaminophen or Ibuprofen in age and weight appropriate dose at proper intervals and duration. Guaifenesin is not included.

2. Children Above Two:
E.g. six year old with upper and lower respiratory infection, nasal congestion, and cough:
Effectively treated with a combination: Cetirizine and Guaifenesin alone or with Acetaminophen or Ibuprofen if there is evidence of fever or pain.

3. Adult:
E.g. thirty year old male with "Flu-like symptoms" i.e. body aches and pains, fever, nasal congestion, difficulty sleeping due to cough, and fatigue during the day.
Effectively treated with combination: Fexofenadine, Ibuprofen, and Guaifenesin in the morning.

4. Elderly Above Seventy:
E.g. seventy five year old female with upper respiratory infection, cough, body aches, fever. No history of liver disease.
Effectively treated with a combination: Fexofenadine, Acetaminophen, and Guaifenesin both morning and before bed.

Representative Samples of Clinical Cases of Patients of Varying Ages Treated by a Doctor, with Non or Minimally Sedating Antihistamines for Cold, Cough and Other Symptoms of Respiratory Infection:

The following clinical treatments were carried out in a doctor's office with the details showing the efficacy of using specific non or minimally sedating antihistamines for effective treatment of cold, cough and other respiratory infections in patients of various ages, as indicated.

Case 1

A 54 year old white male with a complaint of "nose and ear congestion for 8 days", initially received Levaquin, Medrol, and Fexofenadine/pseudoephedrine from a primary care physician with some improvement, but remained symptomatic. A physical exam revealed that the patient's nose was congested bilaterally and the throat had a slight infection. Diagnosis of Present Illness: Upper Respiratory Infection (URI/cold) and prescribed Cetirizine 10 mg QHS, used with Triamcinolone Nasal Spray, with rapid relief of URI symptoms.

Case 2
The same patient as Case 1, at a later time, with a complaint of "cold symptoms for 12 days prior, and sore throat and fever 10 days prior, and a cough for 2 days" and was already taking Triamcinolone Nasal Spray. A further physical exam showed the nose congested with slight erythema bilaterally (consistent with URI). Diagnosis of Present Illness: Upper Respiratory Infection (URI/cold), and Bronchitis. Prescribed Cetirizine 10 mg QHS, with rapid relief of URI symptoms.

Case 3
The same patient as Case 1, at a still later date, with a complaint of "cold symptoms, sore throat 5 days prior". A physical exam showed that the nose was slightly congested and throat slightly infected. Diagnosis of Present Illness: Upper Respiratory Infection (URI/cold). Prescribed Cetirizine 10 mg QHS, with rapid relief of URI symptoms Case 4
A 37 year old African American male with complaint of "slight cold and sore throat, swollen gland on right side of neck for 1 week". Diagnosis of Present Illness: Upper Respiratory Infection (URI/cold). A physical exam showed the nose congested bilaterally and throat slightly infected. Prescribed Fexofenadine 180 mg QD, Triamcinolone Nasal Spray, with rapid relief of URI symptoms Case 5
A 6 year old Asian male child with complaint of "fever 6 days prior". The pediatrician prescribed antibiotic and cough medicine of Carbinoxamine with Dextromethorphan with some improvement shown. A physical exam showed the nose congested bilaterallyDiagnosis of Present Illness: Upper Respiratory Infection (URI/cold). Carbinoxamine with Dextromethorphan were discontinued and prescribed Levocetirizine 2.5 mg at bedtime with rapid relief of URI symptoms Case 6
The same patient as Case 5, with a later complaint of "cough 2 to 3 times per day since stopped Levocetirizine 1 week prior". A physical exam showed nose congested bilaterally with the left side greater than the right but better. Diagnosis of the present illness: Upper Respiratory Infection (URI/cold). Resumed Levocetirizine treatment with 2.5 mg at bedtime with rapid relief of cough.

Case 7
The same patient as Case 6 but with additional complaint of sore throat for 3 days, fever 102° F. yesterday. The patient was using Mometasone Nasal Spray and asthma inhaler, Montelukast. A physical exam showed the nose slightly irritated bilaterally and the throat slightly infected. Diagnosis of Present Illness: Pharyngitis, Upper Respiratory Infection (URI/cold). Resumed Levocetirizine 2.5 mg at bedtime with rapid relief of URI symptoms.

Case 8
A 58 year old white male with "cough, sneezing, and nasal congestion for 3 days". A physical exam showed the nose congested bilaterally and throat slightly infected. Diagnosis of Present Illness: Upper Respiratory Infection (URI/cold)/Allergic Rhinitis. Prescribed Cetirizine 10 mg QHS, with rapid relief of URI symptoms.

Case 9
The same patient as Case 8 with "cough, sneezing, and nose running for 2 days". A physical exam showed nose congested bilaterally. Diagnosis of Present Illness: Upper Respiratory Infection (URI/cold)/Bronchitis, Allergic Rhinitis. Prescribed Cetirizine 10 mg QHS, and Amoxicillin Clavulanate with rapid relief of URI and Bronchitis symptoms.

Case 10
An elderly 77 year old African American male with complaint of "throat hurts since 2 days". A physical exam showed nose congested bilaterally and throat infected. Diagnosis of Present Illness: Pharyngitis, Asthma, COPD. Prescribed Fexofenadine 180 mg QD, Amoxicillin Clavulanate, Prednisone, with rapid relief of Pharyngitis and Bronchitis symptoms.

Case 11
A 60 year old white female with complaint of "nose running and head heavy since yesterday". A physical exam showed nose congested bilaterally, slight bleeding on right, tender frontal and maxillary sinus areas. Throat slight irritated. Diagnosis of Present Illness: Upper Respiratory Infection (URI/cold), "Rule Out" Sinusitis Prescribed Fexofenadine 60 mg BID, Amoxicillin Clavulanate with rapid relief of URI and Sinusitis symptoms.

Case 12
The same patient as Case 11 with complaint of "head heavy since 3 days". A physical exam showed nose slightly congested bilaterally and throat slightly irritated. Diagnosis of Present Illness: Allergic Rhinitis/Upper Respiratory Infection (URI/cold). Prescribed Fexofenadine 60 mg BID with rapid relief of URI symptoms.

Case 13
The same patient as Cases 11 and 12 with complaint of "sore throat since 2 days". A physical exam showed throat slightly irritated. Diagnosis of Present Illness: Upper Respiratory Infection (URI/cold). Prescribed Fexofenadine 60 mg BID with rapid relief of URI symptoms.

Case 14
A 3 year old African American female with complaint of "upper respiratory infection" since today. A physical exam showed the nose congested bilaterally. Throat slightly irritated. Diagnosis of Present illness: Upper Respiratory Infection (URI) Prescribed Cetirizine Liquid 2.5 mg QHS with rapid relief of URI symptoms.

Case 15
A 9 year old African American female with complaint of "fever, sore throat since yesterday". Prescribed Azithromycin by Pediatrician. A physical exam showed the nose slight congested bilaterally and throat slight injected. Diagnosis of Present Illness: Upper Respiratory Infection (URI/Pharyngitis). Prescribed Loratidine 10 mg QD with rapid relief of URI symptoms.

The above case studies indicate that treatment of colds, coughs, flu, and sinus symptoms with non-sedating antihistamines is as effective as the present common treatments with decongestants and sedating antihistamines and accordingly the methods and formulations of the present invention are possible with both effectiveness and safety according to age groups and medical conditions.

It is understood that the examples of specific medications provided are exemplary in nature and that other medications having operational and safety characteristics are within the scope of the present invention as defined in the following claims.

What is claimed is:

1. A method for safely and effectively treating cold, cough, flu, runny nose and sinus symptoms in patients only with respiratory infection, patients ranging in age groups from six month to two years, from two years to six years, from six years to seventy years, and above seventy years in need of treatment, the method comprising the steps of:
   i) ascertaining the age, symptoms, and medical condition of a particular patient to properly categorize the patient within the method;

ii) formulating a medication for treatment of cold, cough, flu, and sinus symptoms, the medication consisting essentially of a combination of materials selected from the group consisting of nonsedating or minimally sedating antihistamines, pain relievers and guaifenesin, the materials being selected according to the ascertained age, symptoms, and medical condition of the patient, wherein elements of the combination of the medication are all recognized as being safe for the patient, and wherein the combination contains one of said antihistamines;

iii) excluding any decongestants, dextromethorphan and sedating antihistamines, aside from minimally sedating antihistamines, from the medication; and iv) treating the patient with the medication with a dose recognized as being effective and safe for the patient according to the patient's age, and medical history, for a time sufficient to alleviate the symptoms of the cold, cough, flu, and sinus symptoms in the patient; wherein the non-sedating or minimally sedating antihistamine is selected from the group consisting of cetirizine, levocetirizine, desloratadine, loratadine, and fexofenadine and wherein the pain reliever is selected from the group consisting of ibuprofen and acetaminophen;

wherein when the patient's age is six months to two years the medication consists essentially of cetirizine or desloratadine;

wherein if the patient is two years to six years old, the medication consists essentially of cetirizine, loratadine, desloratadine or fexofenadine, and if there is evidence in the patient of fever or pain the medication further comprises one of acetaminophen or ibuprofen;

wherein if the patient is six years to seventy years old, the medication consists essentially of cetirizine, levocetirizine, loratadine, desloratadine or fexofenadine, with or without guaifenesin, and if there is evidence in the patient of fever or pain, the medication further comprises one of acetaminophen or ibuprofen; and wherein if the patient is above seventy years old, the medication consists essentially of loratadine, desloratadine or fexofenadine, with or without guaifenesin, and if there is evidence in the patient of fever or pain, the medication further comprises acetaminophen.

* * * * *